US011191609B2

(12) United States Patent
McGinley et al.

(10) Patent No.: US 11,191,609 B2
(45) Date of Patent: Dec. 7, 2021

(54) AUGMENTED REALITY BASED REAL-TIME ULTRASONOGRAPHY IMAGE RENDERING FOR SURGICAL ASSISTANCE (71) Applicant: MCGINLEY EDUCATION INNOVATIONS, LLC, Casper, WY (US)

(72) Inventors: Joseph McGinley, Casper, WY (US); Suresh Muknahallipatna, Laramie, WY (US); Bradley Riotto, Laramie, WY (US); John McInroy, Laramie, WY (US)

(73) Assignees: The University of Wyoming, Laramie, WY (US); McGinley Education Innovations, LLC, Casper, WY (US)

( * ) Notice: Subject to any disclaimer, the term of this patent is extended or adjusted under 35 U.S.C. 154(b) by 0 days.

(21) Appl. No.: 16/635,505

(22) PCT Filed: Oct. 8, 2019

(86) PCT No.: PCT/US2019/055237
§ 371 (c)(1),
(2) Date: Jan. 30, 2020

(87) PCT Pub. No.: WO2020/076856
PCT Pub. Date: Apr. 16, 2020

(65) Prior Publication Data
US 2021/0045837 A1 Feb. 18, 2021

Related U.S. Application Data (60) Provisional application No. 62/742,735, filed on Oct. 8, 2018.

(51) Int. Cl.
*A61B 90/00* (2016.01)
*A61B 90/50* (2016.01)
(Continued)

(52) U.S. Cl.
CPC .............. *A61B 90/37* (2016.02); *A61B 90/50* (2016.02); *G06T 19/006* (2013.01); *G06T 19/20* (2013.01);
(Continued)

(58) Field of Classification Search
CPC ..... A61B 90/37; A61B 90/50; A61B 2010/41; A61B 2090/365; A61B 2090/378; A61B 2090/502; G06T 19/20; G06T 19/006
See application file for complete search history.

(56) References Cited

U.S. PATENT DOCUMENTS 5,912,720 A 6/1999 Berger
6,351,573 B1 2/2002 Schneider
(Continued)

FOREIGN PATENT DOCUMENTS

WO 2016207628 12/2016

OTHER PUBLICATIONS

Traub et al., "Advanced Display and Visualization Concepts for Image Guided Surgery", Journal of Display Technology, vol. 4, No. 4, Dec. 2008, pp. 483-490 (Year: 2008).*
(Continued)

*Primary Examiner* — Nay A Maung
*Assistant Examiner* — Jose M Torres
(74) *Attorney, Agent, or Firm* — Holzer Patel Drennan (57) ABSTRACT Use of augmented reality to provide a real-time two-dimensional representation of medical imaging data to a user in a three-dimensional space. An augmented reality system is discussed that may provide a single stage processing for video data ingestion directly from a video data output of a medical imaging device. In turn, latency in the resulting video data presented to the user via an augmented reality display may be reduced. The augmented reality system may also allow for a high degree of control over the virtual (Continued)

position, rotation, size, and/or opacity of the two-dimensional representation of the video data in the three-dimensional space associated with the augmented reality system.

21 Claims, 6 Drawing Sheets (51) Int. Cl.
G06T 19/00 (2011.01)
G06T 19/20 (2011.01)

(52) U.S. Cl.
CPC ... A61B 2090/365 (2016.02); A61B 2090/378 (2016.02); A61B 2090/502 (2016.02); G06T 2210/41 (2013.01)

(56) References Cited

U.S. PATENT DOCUMENTS

| | | | |
|---|---|---|---|
| 6,599,247 | B1 | 7/2003 | Stetten |
| 6,669,635 | B2 | 12/2003 | Kessman |
| 6,847,336 | B1 | 1/2005 | Lemelson |
| 6,891,518 | B2 | 5/2005 | Sauer |
| 6,919,867 | B2 | 7/2005 | Sauer |
| 7,002,551 | B2 | 2/2006 | Azuma |
| 7,079,132 | B2 | 7/2006 | Sauer |
| 7,176,936 | B2 | 2/2007 | Sauer |
| 7,607,079 | B2 | 10/2009 | Reiner |
| 7,714,895 | B2 | 5/2010 | Pretlove |
| 9,123,155 | B2 | 9/2015 | Cunningham |
| 9,767,608 | B2* | 9/2017 | Lee ................ A61B 1/00149 |
| 10,010,379 | B1* | 7/2018 | Gibby ................ A61B 90/90 |
| 2002/0082498 | A1 | 6/2002 | Wendt et al. |
| 2003/0229282 | A1 | 12/2003 | Burdette et al. |
| 2006/0176242 | A1 | 8/2006 | Jaramaz et al. |
| 2006/0181482 | A1 | 8/2006 | Iaquinto |
| 2011/0107270 | A1* | 5/2011 | Wang ................ G16H 20/40 715/850 |
| 2011/0236868 | A1 | 9/2011 | Bronstein et al. |
| 2013/0038707 | A1* | 2/2013 | Cunningham ....... A61B 1/0005 348/65 |
| 2013/0293578 | A1* | 11/2013 | Leung ................ G06F 3/147 345/633 |
| 2014/0198190 | A1 | 7/2014 | Okumu |
| 2014/0228653 | A1 | 8/2014 | Kiraly |
| 2014/0275760 | A1 | 9/2014 | Lee et al. |
| 2014/0303491 | A1 | 10/2014 | Shekhar et al. |
| 2015/0297062 | A1 | 10/2015 | Golenberg |
| 2016/0191887 | A1 | 6/2016 | Casas |
| 2016/0225192 | A1 | 8/2016 | Jones et al. |
| 2017/0042631 | A1 | 2/2017 | Doo et al. |
| 2017/0103440 | A1 | 4/2017 | Tian |
| 2017/0323472 | A1* | 11/2017 | Barnes ................ G06K 9/6251 |
| 2017/0345398 | A1 | 11/2017 | Fuchs et al. |
| 2017/0360402 | A1 | 12/2017 | de Jonge et al. |
| 2018/0012416 | A1* | 1/2018 | Jones ................ A61B 34/10 |
| 2018/0070113 | A1 | 3/2018 | Phillips et al. |
| 2018/0260931 | A1 | 9/2018 | Ozguner et al. |
| 2019/0295496 | A1* | 9/2019 | Wagner ................ G09G 5/02 |
| 2019/0310819 | A1* | 10/2019 | Xu ................ G16H 30/40 |
| 2020/0105070 | A1* | 4/2020 | Coustaud ................ G06T 19/20 |
| 2020/0265754 | A1* | 8/2020 | Buras ................ A61B 5/0002 |
| 2020/0302694 | A1* | 9/2020 | Flexman ................ G06F 3/017 |

OTHER PUBLICATIONS

Cutolo et al., "Video See Through AR Head-Mounted Display for Medical Procedures", IEEE International Symposium on Mixed and Augmented Reality 2014, Science and Technology Proceedings, Sep. 10-12, 2014, pp. 393-396 (Year: 2014).*

Bajura et al., "Merging Virtual Objects with the Real World: Seeing Ultrasound Imagery within the Patient", Computer Graphics, 26, 2, Jul. 1992, pp. 203-210 (Year: 1992).*

Kersten-Oertel et al., "The state of the art of visualization in mixed reality image guided surgery", Computerized Medical Imaging and Graphics 37 (2013), pp. 98-112 (Year: 2013).*

"Advanced Display and Visualization Concepts for Image Guided Surgery", Joerg Traub et al., Journal of Display Technology, vol. 4, No. 4, Dec. 2008.

"Bringing Virtual Reality to Medical Treatment", Andrea K. McDaniels,, The Baltimore Sun, 2017 Article and Video. https://www.baltimoresun.com/health/bs-hs-virtual-reality-medicine-20170508-story.html.

"A High-Accuracy Surgical Augmented Reality System Using Enhanced Integral Videography Image Overlay", Zhang X. et al., 2015 Article.

"Video See Through AR Head-Mounted Display for Medical Procedures", Fabrizio Cutolo et al., 2014, IEEE.

"Augmented Reality in Surgery", Jeffrey H. Shuhaiber. 2004 Article.

Blackwell et al., An image overlay system for medical data visualization, 1998, Kanade Proceedings of the 1998 Medical Imaging computing and Computer Assisted Intervention Conference (MICCAI '98).

Merging Virtual Objects With the Real World: Seeing Ultrasound Imagery Within the Patient, Computer Graphics, vol. 26, pp. 203-210, 1992, Bajura et al.

"A Medical Revolution" Microsoft, 2017 Article.

Ferrari, Vincenzo, Mauro Ferrari, and Franco Mosca. "Video see-through in the clinical practice." EICS4Med 2011 (2011 ).

Kersten-Oertel, Marta, Pierre Jannin, and D. Louis Collins. "The state of the art of visualization in mixed reality image guided surgery." Computerized Medical Imaging and Graphics 37.2 (2013): 98-112.

"Wyoming Medical Society's 'Future of Medicine' Showcases Latest in Medical Technology", St. John's Health., 2018 Webpage.

* cited by examiner

AUGMENTED REALITY BASED REAL-TIME ULTRASONOGRAPHY IMAGE RENDERING FOR SURGICAL ASSISTANCE

RELATED APPLICATIONS

This application is a U.S. National Stage under 37 CFR 1.371 of PCT/US2019/055237 filed on Oct. 8, 2019, entitled "AUGMENTED REALITY BASED REAL-TIME ULTRASONOGRAPHY IMAGE RENDERING FOR SURGICAL ASSISTANCE", which claims the benefit of U.S. Provisional Patent Application No. 62/742,735 filed Oct. 8, 2018, entitled "AUGMENTED REALITY BASED REAL-TIME ULTRASONOGRAPHY IMAGE RENDERING FOR SURGICAL ASSISTANCE," which is incorporated herein by reference in its entirety.

FIELD

The present disclosure generally relates to medical imaging, and specifically to the use of augmented reality in connection with medical imaging for presentation of medical imaging to a medical provider.

BACKGROUND

Medical imaging is often used by medical providers in conjunction with provision of medical care. Specifically, preoperative medical imaging may assist medical providers in delivery of care to a patient. This may include assistance during surgical operations, treatments, or other procedures. Currently, medical imaging techniques may be used to provide real-time two-dimensional images during an interventional procedure. This technique is described as intraoperative imaging. Typically, the two-dimensional images depict the relative position of anatomic structures and/or surgical tools or other instruments. Presentation of the images in this manner may allow a user to plan and guide surgical equipment more reliably during an interventional procedure. The images are displayed on a computer or video monitor positioned adjacent to the patient. In turn, a user may be required to avert his or her attention from the patients to the monitors to observe the intraoperative imaging presented on the computer or video monitor. During this repeated back and forth viewing of the patient and monitor, the user is also expected to mentally correlate the two-dimensional images with the three-dimensional structure of the actual patient.

However, the repeated back-and-forth movement of the user's attention between the patient and the monitor leads to fatigue and other potential safety concerns. Moreover, it may be challenging for a user to mentally relate to the positions depicted in the two-dimensional rendering of the medical imaging relative to the three-dimensional anatomy of the patient.

In turn, approaches have been proposed in which alternative means for provision of medical imaging to a medical care provider are provided. These have included use of augmented reality to present medical imaging to a medical care provider. Augmented reality devices allow for presentation of virtual or digital information to a user while observing the real-world environment in which the user is positioned. While a number of approaches to augmented reality have been contemplated, challenges remain in relation to successful implementation of an intraoperative imaging approach using augmented reality. Therefore, the need remains for improved techniques for use of augmented reality in connection with presentation of medical imaging to a medical care provider during provision of medical care to facilitate improved intraoperative imaging for improved patient outcomes.

SUMMARY

The present disclosure recognizes a number of challenges present in the previously contemplated approaches to use of augmented reality in connection with medical imaging. The present inventors recognize that latency in the presented medical imaging is a significant challenge in connection with provision of intraoperative imaging. Specifically, augmented reality involves use of significant computational resources in connection with presentation of virtual or digital data to a user. Given the context of intraoperative imaging, it may be desirable that the medical imaging presented to a user be real-time or as near real-time as possible. Accordingly, while prior approaches contemplated use of medical imaging obtained prior to operation and stored in a data repository for later retrieval, these approaches are limited in that the medical care provider is not provided with the most up-to-date medical imaging reflective of the real-time condition of the anatomy of the patient. This leads to disadvantages that limited the applicability of such approaches that use stored data for presentation to a user.

Moreover, the present inventors recognize that incorporation of real-time video data into an augmented reality environment using traditional approaches resulted in significant latency in the video data comprising the medical imaging. For instance, real-time medical imaging such as ultrasound images, computed tomography (CT) images, magnetic resonance imaging (MRI) images, or other medical imaging approaches that generate video data that, when processed in connection with an augmented reality system, result in significant latency between the presented video data stream and the real-time treatment of the patient. Processing such data often involved multi-stage handling by a plurality of computer systems and/or programs, each introducing latency into the resulting video data presented to the user.

Accordingly, the present disclosure presents configurations of an augmented reality system for use in presentation of real-time medical imaging data in the form of a video data stream such that the medical imaging data is presented with reduced latency for more synchronous coordination of the presented medical imaging and the real-world environment in which the user operates. One approach described herein generally includes direct interface between an augmented reality engine and a source of a medical imaging video data stream. As used herein, an augmented reality engine comprises a collection of computational resources utilized in presenting augmented reality data to a user. In this regard, the augmented reality engine may include hardware, software, and firmware in any combination. Specifically, the augmented reality engine may include memory and one or more processors. Furthermore, the augmented reality engine may include non-transitory machine-readable instructions stored in memory that are executable by a processor to achieve certain functionality described herein. The augmented reality engine may include utilization of a central processing unit (CPU), graphics processing unit (GPU), or any other appropriate hardware for execution of the augmented reality engine to achieve the functionality described herein.

In contrast to the embodiments described herein, prior approaches to augmented reality typically rely on intermediary processing between the source of the data to be presented and the augmented reality engine (e.g., for initial data ingestion, processing, translation, and/or standardization). For instance, the computing device executing the augmented reality engine may initially process any input data through graphics processing resources of the host device prior to passing any such data to the augmented reality engine for processing in connection with the augmented reality system. However, as this intermediary processing results in latency introduced in the video data presented to the user using the augmented reality system, direct interface is advantageous to reduce such latency.

Specifically, one approach described herein includes a script executable directly by the augmented reality engine for direct ingestion of a video data stream for processing by the augmented reality engine for presentation in an augmented reality display device. Such script may be cacheless. That is, typically during augmented reality processing a data cache may be provided to buffer a video stream data to preserve video stream data quality or provide other compensation for potential data errors in the video stream to be presented. However, it has been found that the reduction latency achieved by operating in a cacheless context may outweigh the benefits to video quality presented by use of a data cache. Moreover, as the resolution of medical imaging data may be often relatively low as compared to other video data stream sources contemplated for use in augmented reality, such as high-resolution (e.g., 4K resolution) gaming objects, video streams, or other data streams, the requirement of the data cache may be reduced as the incidence of data errors may be reduced given the relatively low bandwidth requirements of many medical imaging video data streams.

Furthermore, prior approaches to utilization of augmented reality for presentation of medical imaging suffer from drawbacks in the limited ability to manipulate the manner in which the video data of medical imaging data is presented to the user. However, the present application provides a robust video stream manipulation capability that allows customization or tailoring of the manner in which the video data is presented to the user in the augmented reality hardware. This may allow a given user to manipulate the manner in which the video data is presented in the augmented reality headset for use in different operational contexts. This may also facilitate different users having different preferences on how the video data is displayed to customize the display to the preferences of the users.

The video data may be manipulated within a three-dimensional space defined relative to the augmented reality display device utilized by the user. That is, a three-dimensional space may be defined within the field of view of a user. The video data may be represented as a two-dimensional video window within the three-dimensional space. The two-dimensional video data displayed within the three-dimensional space defined in the field of view may be manipulated in any number of different manners. For example, at least one degree of translational freedom may be provided such that the video data be moved in a given direction within the three-dimensional space. In a preferred embodiment, three degrees of translational freedom may be provided such that the video data presented to the user may be translated freely within the three-dimensional space. For instance, in relation to a depth dimension corresponding to moving the two-dimensional representation of the video data nearer and further from the user, the video may be scaled to give the illusion or perspective of depth. Further still, the video data may have at least one degree of rotational freedom within the three-dimensional space. In this regard, the two-dimensional representation of video data within the three-dimensional space may be freely rotated about the rotational degree of freedom provided. Preferably, three degrees of rotational freedom may be provided such that the two-dimensional representation of the video data to be rotated about three axes relative to the three-dimensional space.

Further still, the relative size of the two-dimensional representation of the video data may be altered by the user such that the video may be scaled in the different relative sizes within the three-dimensional space. Also, a transparency value or opacity of the two-dimensional representation of the video data may be controlled by the user such that the opacity of the video data may be reduced to allow for simultaneous viewing of the video data with other portions of the visual field "behind" or distal to the video data relative to the user within three-dimensional space.

In turn, the ability to customize or manipulate the two-dimensional representation of the video data in the three-dimensional space may allow a user to position the video data relative to the patient. For example, a user may position the two-dimensional representation of the video stream adjacent to the patient to allow for simultaneous viewing of the video data comprising the medical imaging while also viewing the patient. Further still, the user may, in effect, superimpose the two-dimensional representation of the video data comprising the medical imaging relative to the real-world anatomy of the patient. This may assist the user in visualizing relevant anatomy and assist in providing guidance during an operation.

In view of the foregoing, a first embodiment relates to an augmented reality system for presentation of real-time medical imaging data to a user. The system includes an augmented reality engine executed by one or more processors (e.g., including CPU and/or GPU configurations) and in direct operative communication with a video data output of a medical imaging device. The augmented reality engine is also in operative communication with an augmented reality display device. The system further includes a data ingestion script executable by the processor of the augmented reality engine for receipt of the video data output of the medical imaging device. The data ingestion script executes without a data cache in which the video data output is stored prior to processing for communication to the augmented realty display device such that the video data output. The system also includes a video manipulation module operative to control at least a position of a two-dimensional representation of the video data output in a three-dimensional space relative to the augmented reality display device at least with respect to one degree of translational freedom and at least with respect to at least one rotational degree of freedom in the three-dimensional space.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, in an embodiment, the data ingestion script may directly receive the video data output from a graphics card of the medical imaging device without intervening processing. The medical imaging device may include one of an ultrasound device, an MRI device, a CT device, or other appropriate medical imaging device. In a specific embodiment, the medical imaging device may be an ultrasound device (e.g., for real-time capture of ultrasound imaging data). The data ingestion script may be operative to receive the video data output in a format corresponding to a video interface. For instance, the video interface may comprise at least one of DVI, HDMI, VGA, or other appropriate standard or proprietary video output format.

In an embodiment, the video manipulation module may be operative to control the position of the two-dimensional representation of the video data output in at least two translational degrees of freedom in the three-dimensional space. In a further embodiment, the video manipulation module may be operative to control the position of the two-dimensional representation of the video data output in at least three translational degrees of freedom in the three-dimensional space. Further still, the video manipulation module may be operative to control the position of the two-dimensional representation of the video data output in at least two rotational degrees of freedom in the three-dimensional space. In another embodiment, the video manipulation module may be operative to control the position of the two-dimensional representation of the video data output in at least three rotational degrees of freedom in the three-dimensional space.

In addition, the video manipulation module may be operative to control a size of the two-dimensional representation of the video data output in the three-dimensional space. The video manipulation module may be operative to control an opacity of the two-dimensional representation of the video data output in the three-dimensional space.

In an embodiment, the system may further include an augmented reality display device comprising a wearable display positionable in a visual field of a user wearing the augmented reality display. The augmented reality display is operative to display to the user the two-dimensional representation of the video data output. The video manipulation module may be operative to generate a menu for display in the three-dimensional space for receipt of user inputs to control at least the position of the two-dimensional representation of the video data output in the three-dimensional space.

A second aspect relates to a method for presenting medical imaging data to a user in an augmented reality environment. The method includes receiving video data output at a data ingestion script of an augmented reality engine via direct communication with a medical imaging device and processing the video data output by the augmented reality engine in real time in a cacheless environment. The method further includes determining a position of a two-dimensional representation of the video data output in a three-dimensional space relative to an augmented reality display device. The determining includes controlling the position of the two-dimensional representation of the video data output in the three-dimensional space in at least one degree of translational freedom and at least with respect to at least one rotational degree of freedom in the three-dimensional space. Furthermore, the method includes communicating data corresponding to the two-dimensional representation of the video data output to the augmented reality display device.

A number of feature refinements and additional features are applicable to the second aspect. These feature refinements and additional features may be used individually or in any combination. As such, each of the following features that will be discussed may be, but are not required to be, used with any other feature or combination of features of the second aspect.

For instance, the determining may include controlling the position of the two-dimensional representation of the video data output in the three-dimensional space in three degree of translational freedom. Further still, the determining may include controlling the position of the two-dimensional representation of the video data output in the three-dimensional space in three degree of rotational freedom.

In a further embodiment, the method may include controlling a size of the two-dimensional representation of the video data output in the three-dimensional space. Additionally or alternatively, the method may include controlling an opacity of the two-dimensional representation of the video data output in the three-dimensional space. The method may include presenting a menu to a user via the augmented reality display device. The menu may include at least one interactive element corresponding to the position of the two-dimensional representation of the video output data in the three-dimensional space. As such, the method may further include receiving a user selection regarding the position of the two-dimensional representation of the video output data in the three-dimensional space and outputting data corresponding to the user selection to the augmented reality display device.

A third aspect relates to a non-transitory computer readable medium comprising machine readable instructions, that when executed by a processor of an augmented reality engine, cause the processor to receive video data output at a data ingestion script of an augmented reality engine via direct communication with a medical imaging device and process the video data output by the augmented reality engine in real time in a cacheless environment. The processor is also configured by the instructions to determine a position of a two-dimensional representation of the video data output in a three-dimensional space relative to an augmented reality display device. The determining includes controlling the position of the two-dimensional representation of the video data output in the three-dimensional space in at least one degree of translational freedom and at least with respect to at least one rotational degree of freedom in the three-dimensional space. Furthermore, the instructions cause the processor to communicate data corresponding to the two-dimensional representation of the video data output to the augmented reality display device.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1:
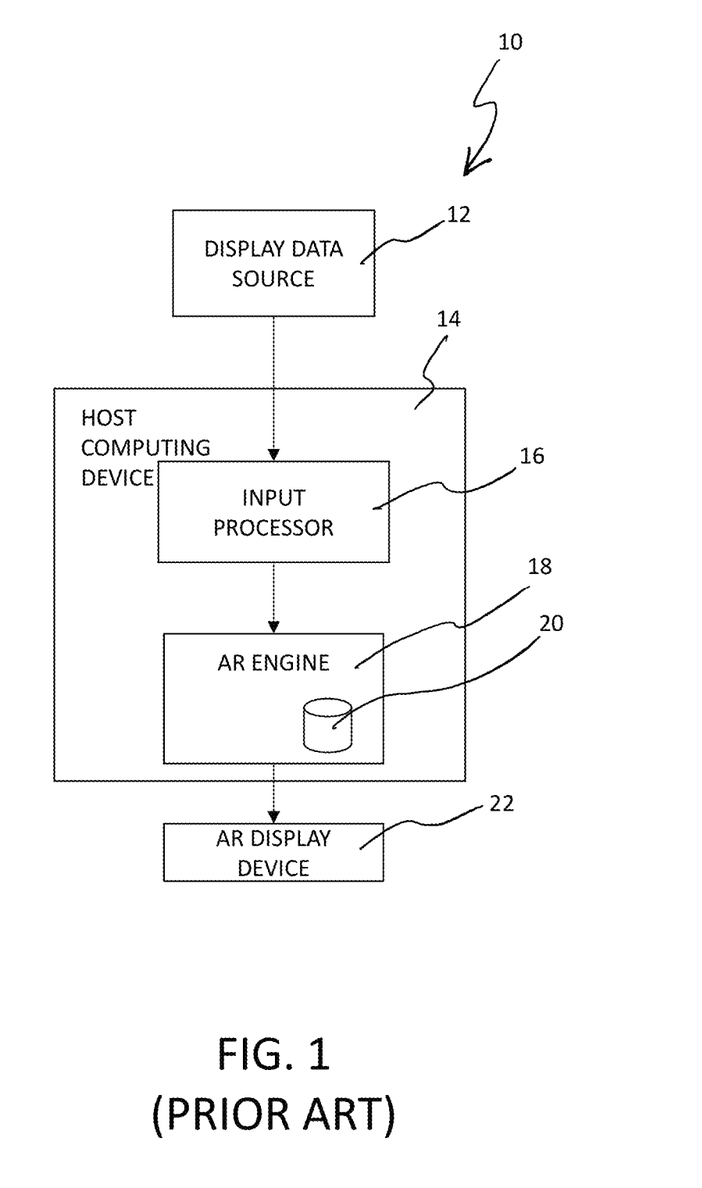
FIG. 1 depicts a prior art approach to processing of data for presentation in augmented reality display device.

FIG. 1 depicts a prior art approach to an augmented reality system 10. The augmented reality system 10 includes a display data source 12, a host computing device 14, and an augmented reality display device 22. The augmented reality display device 22 may include a wearable device such as a headset, visor, or the like that may include a transparent or translucent portion upon which information is displayed. The transparent or translucent portion may be presented within the field of view of a user such that the user may also view the real-world environment about the user. In this regard, the augmented reality system 10 may be utilized to present information from the display data source 12 to the user by way of the augmented reality display device 22.

The display data source 12 may include an external source of data or may include data generated by a program (e.g., that may be executing on the host computing device 14), locally stored data, or other data to be displayed using the augmented reality display device 22. For example, in many prior art approaches, the display data source 12 may include previously generated or stored data that is stored in memory and accessed by the host computing device 14 for presentation by the augmented reality display device 22. In this regard, the display data source 12 in prior art approaches have included medical imaging data that has been obtained prior to an operation and is stored in a memory for access during the operation or procedure. In other instances, the display data source 12 may include virtual data generated for presentation to the user via the augmented reality display device 22. This regard, the display data source 12 may include a program or other means for generation of virtual or digital data to be displayed to the user.

The host computing device 14 may act as a processor for processing information from the display data source 12 such that the data may be presented to the user by way of the augmented reality display device 22. In this regard, the host computing device 14 may include a computing device including a processor and memory. For instance, the host computing device 14 may comprise a server, desktop computer, laptop computer, or other computing device that provides sufficient processing power to process the data to be presented by way of the augmented reality display device 22. In the prior art approach depicted in FIG. 1, the host computing device 14 of the augmented reality system 10 includes an input processor 16. The host computing device 14 also includes an augmented reality engine 18. In this case, the host computing device 14 may include two-stage data processing in which display data 12 is initially processed by the input processor 16 and in turn pass to the augmented reality engine 18 for further processing of the data prior presentation via the augmented reality display device 22.

For instance, the input processor 16 may include a graphics application program interface (API) that functions as a graphics library for processing of the display data from the display data source 12. This processing may include receipt of display data, storage of that data, with additional processing to be performed on the data such as translation or transformation of the data into a format that is adapted for input to the augmented reality engine 18. In turn, the augmented reality engine 18 may receive the data from the input processor 16 for further processing necessary for interface with the augmented reality display device 22. For instance, the augmented reality engine 18 may include processing such that the display data 12, when presented to the user via the augmented reality display device 22, is rendered correctly. This may include processing based on input from the augmented reality display device 22 in relation to the position of the device 22 in the physical environment, inputs from the user, or other information that may be used in conjunction with the data to be displayed to correctly render the data in the augmented reality display device 22. As such, the augmented reality engine 18 may perform processing to account for spatial considerations and/or processing that accounts for the real-world environment about the user.

In addition, the augmented reality engine 18 may include a data cache 20 with a dedicated amount of memory that is used for buffering data at the augmented reality engine 18 (e.g., prior to processing or prior to transmitting data to the augmented reality display device 22). The use of the data cache 20 may be utilized to prevent data errors that may result in pixilation, judder, or other image defects that may result from inadequate processing capability or other errors in association with the processing of the display data by the augmented reality engine 18.

As described above, the augmented reality system 10 may suffer from a number of drawbacks that are particularly relevant in the application of intraoperative imaging. Specifically, the two-step processing at the host computing device 14 that includes processing by both the input processor 16 and the augmented reality engine 18 may result in latency in the data to be displayed to the user using the augmented reality display device 22. Such latency may be of less concern in instances where the immediacy or currency of the data to be displayed is less critical than it is in the intraoperative imaging contacts.

Figure 2:
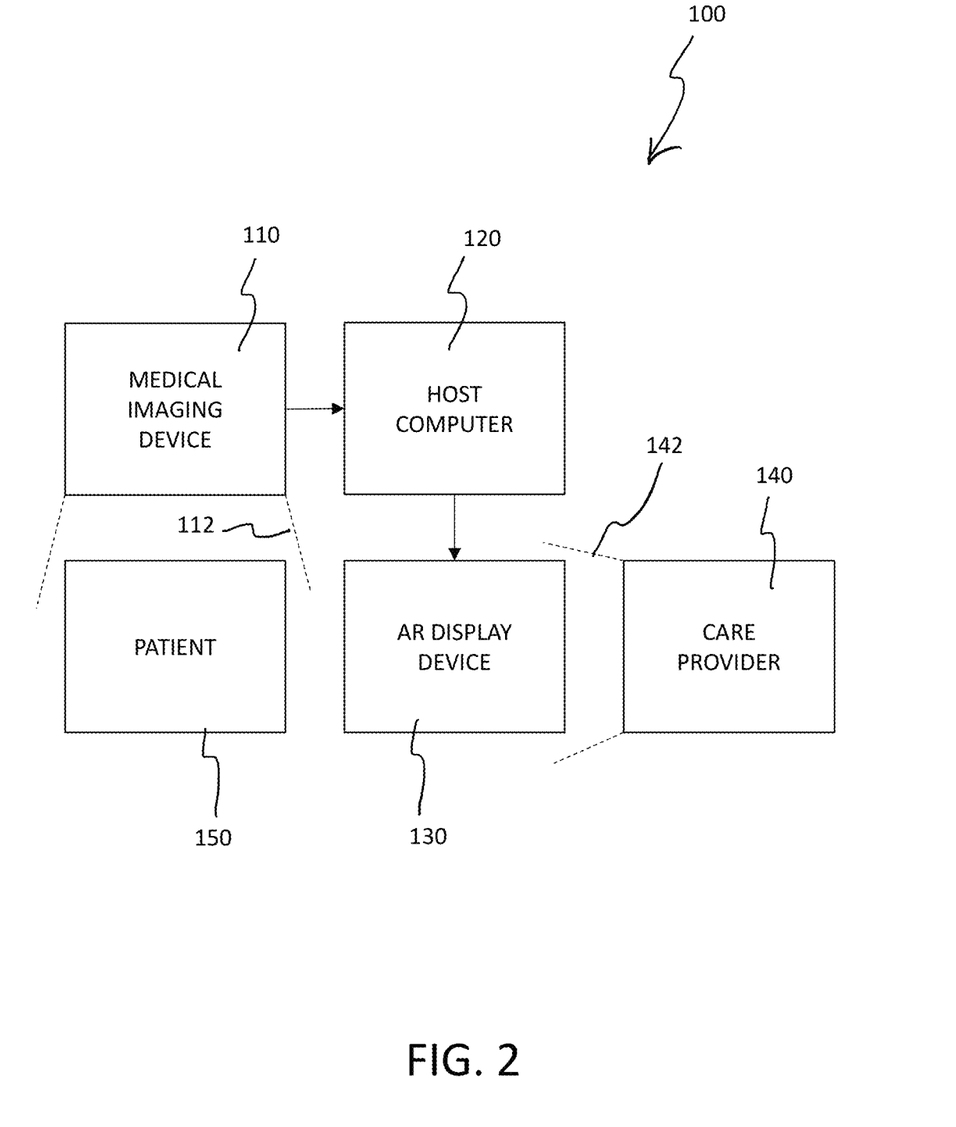
FIG. 2 depicts a schematic view of an embodiment of a system for presentation of medical imaging data in an augmented reality display device.

With further reference to FIG. 2, an intraoperative imaging environment 100 is depicted that may be utilized for presentation of medical imaging to a medical care provider for use during provision of medical care to a patient. As may be appreciated, currency of data in the intraoperative imaging context may be a primary concern to provide the medical care provider real-time imaging data. In the intraoperative imaging environment 100, a medical imaging device 110 may include a field of view 112 that extends to a patient 150 such that anatomy of the patient 150 may be imaged by the medical imaging device 110. In turn, the medical imaging device 110 provides display data to a host computer 120 that in turn provides data to an augmented reality display device 130. The augmented reality display device 130 may be presented in a field of view 142 of a medical care provider 140 that may interface with the augmented reality display device 130 to provide medical care to the patient 150 utilizing the data provided to the medical care provider 140 in the augmented reality display 130.

The medical imaging device 110 may be any appropriate medical imaging device that provides relevant medical imaging data. For instance, the medical imaging device 110 may include an ultrasound device, a CT device, an MRI device, an x-ray device, or any other appropriate device operative to generate medical imaging data.

The augmented reality display device 130 may comprise any appropriate augmented reality display device 130 including wearable displays such as smart glasses, heads up displays, augmented reality helmets, augmented reality headsets, or other appropriate augmented reality displays. For instance, the augmented reality display device 130 may comprise commercially available augmented reality display devices such as the Microsoft® HoloLens, Meta® 2 device, Google® smart glasses, or other appropriate augmented reality display device.

Figure 3:
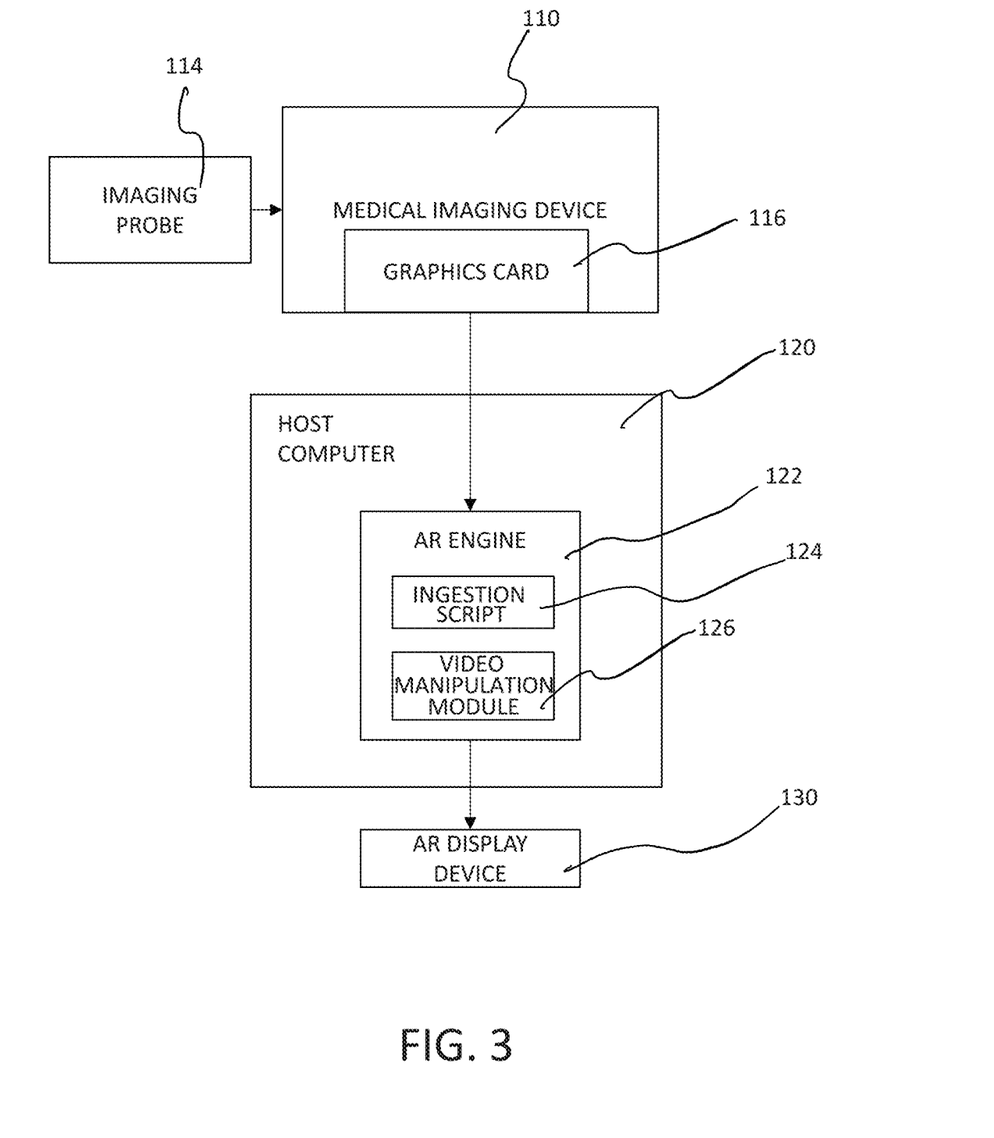
FIG. 3 depicts a schematic view of an embodiment of the system for presentation of medical imaging data in an augmented reality display device with low latency.

In view of the importance of currency of data to be presented using the augmented reality display device 130, the host computer 120 include a specific configuration that provides low latency data display for presentation of real-time medical imaging from medical imaging device 110 to the augmented reality display device 130. With further reference to FIG. 3, the medical imaging device 110 may include a medical imaging probe 114 that may image the field of view 112. In turn, medical imaging data generated by the medical imaging device 110 may be generated and output on a graphics card 116 of the medical imaging device 110. The graphics card 116 may include any appropriate physical output port such as DVI, HDMI, VGA, DisplayPort, or other standardized or proprietary video output port. The data from the graphics card 116 may be provided via the physical port using any standardized or proprietary format associated with the relevant display output technology employed. That is, the medical imaging data may be output by the graphics card 116 in any standardized or proprietary video data stream output. In turn, the host computer 120 may comprise an augmented reality engine 122 that is operative for direct receipt of the medical imaging data from the graphics card 116 of the medical imaging device 110 (e.g., without further processing by other programs/processors of the host computer 120 as is performed in prior art contexts). Accordingly and in contrast to the system described in FIG. 1, the host computer 120 may forgo use of and input processor 16 for initial receipt and processing of the medical imaging data received from the medical imaging device 116.

Rather, the augmented reality engine 122 may execute an ingestion script 124 comprising a specific program script that processes the medical imaging data received directly from the graphics card 116 of the medical imaging device 110. The direct receipt of the medical imaging device from the graphics card 116 may reduce latency in the resulting medical imaging data presented in the augmented reality display device 130. Accordingly, the ingestion script 124 may comprise non-transitory machine readable instructions stored in a memory of augmented reality engine 122. Accordingly, a processor of the augmented reality engine 122 may be operative to read the ingestion script 124 from memory to execute functionality associated therewith.

Moreover, the augmented reality engine 122 and ingestion script 124 of the augmented reality engine 122 may be cacheless such that no data cache is employed when the ingestion script 124 is executed by the augmented reality engine 122. In turn, the augmented reality engine 122 may present data for presentation to the user via the augmented reality display device 130. As the augmented reality engine 122 may directly process the medical imaging data from the graphics card 116 of the medical imaging device 110 without use of a data cache, the medical imaging data presented to the user may have extremely low latency. In this regard, the augmented reality system 100 depicted in FIGS. 2-3 may prioritize low latency over any potential data errors. This may be accomplished as the data bandwidth of the medical imaging data received from medical imaging device 110 may be relatively low such that the likelihood of processing errors of the data in the augmented reality engine 122 are low. That is, the nature of the data may be such that the processing capability of the augmented reality engine 122 is sufficient to process the data without any data errors. Moreover, to the extent that any data errors occur, any potential short-term image defects resulting from such errors may be of less concern than providing medical imaging data with low latency.

Figure 4:
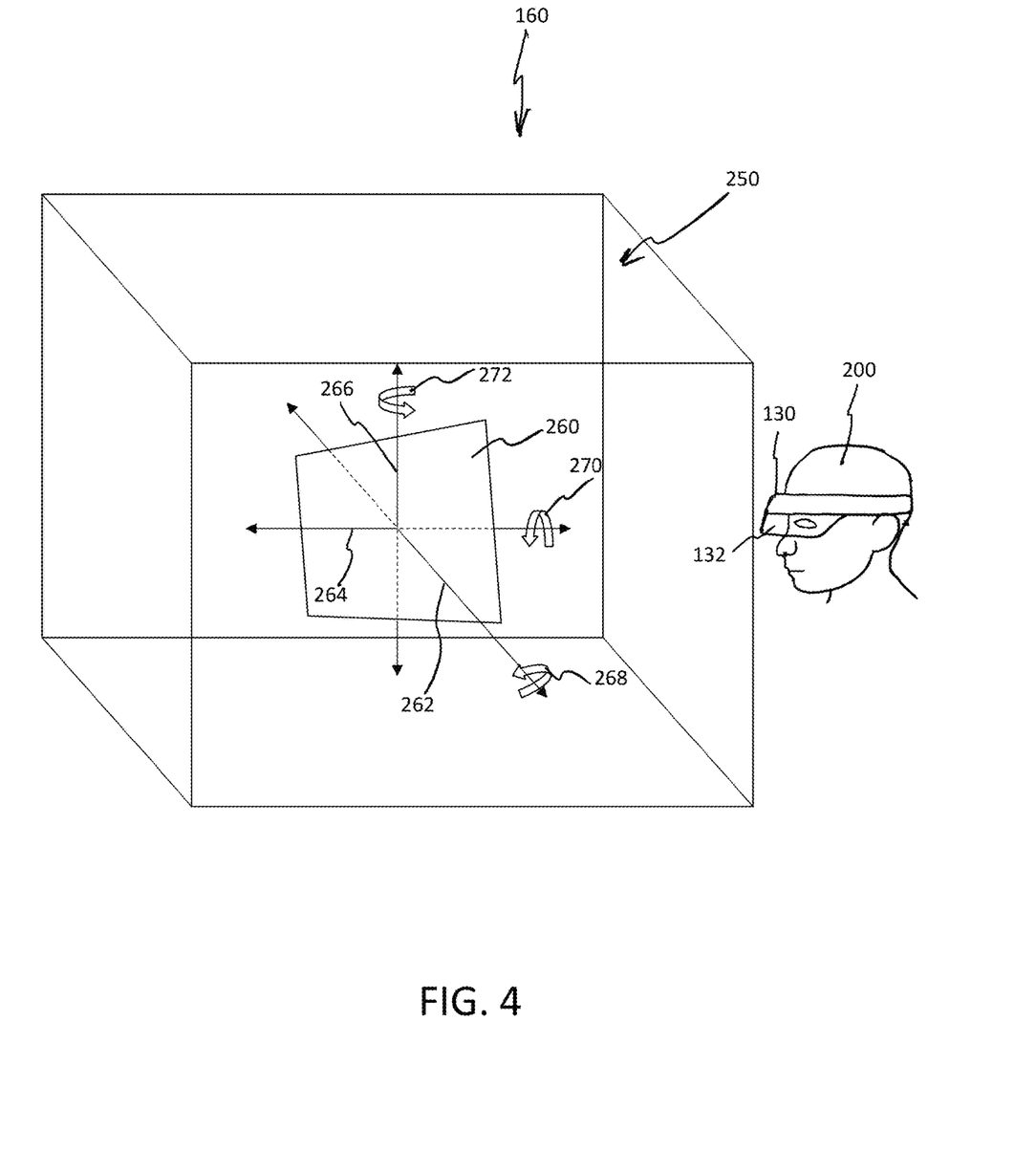
FIG. 4 depicts an embodiment of a three-dimensional environment defined relative to an augmented reality display device worn by the user in which a two-dimensional representation of video data is configurable for presentation to the user within the three-dimensional space.

With additional reference to FIG. 4, a representation of an augmented reality environment 160 is depicted. As may be appreciated, a user 200 may wear an augmented reality display device 130 that includes a transparent display 132 positioned relative to the user 120 such that the transparent display 132 may be in a field of view of the user 200. In turn, a three-dimensional environment 250 may be represented in the field of view of the user 200. The host computer 120 may be operative to generate a two-dimensional display 260 of medical imaging data that is presented within the three-dimensional environment 250. That is, the augmented reality display device 130 may display data on the transparent display 130 such that it appears to the user 200 that the two-dimensional representation 260 appears in the three-dimensional environment 250.

Specifically, the augmented reality engine 120 may also include a video manipulation module 126. The video manipulation module may comprise non-transitory, machine readable instructions that may be executed by a processor of the augmented reality engine 120. Specifically, the video manipulation module may process the video output data to render the two-dimensional representation 260 relative to the three-dimensional environment 250.

Figure 5:
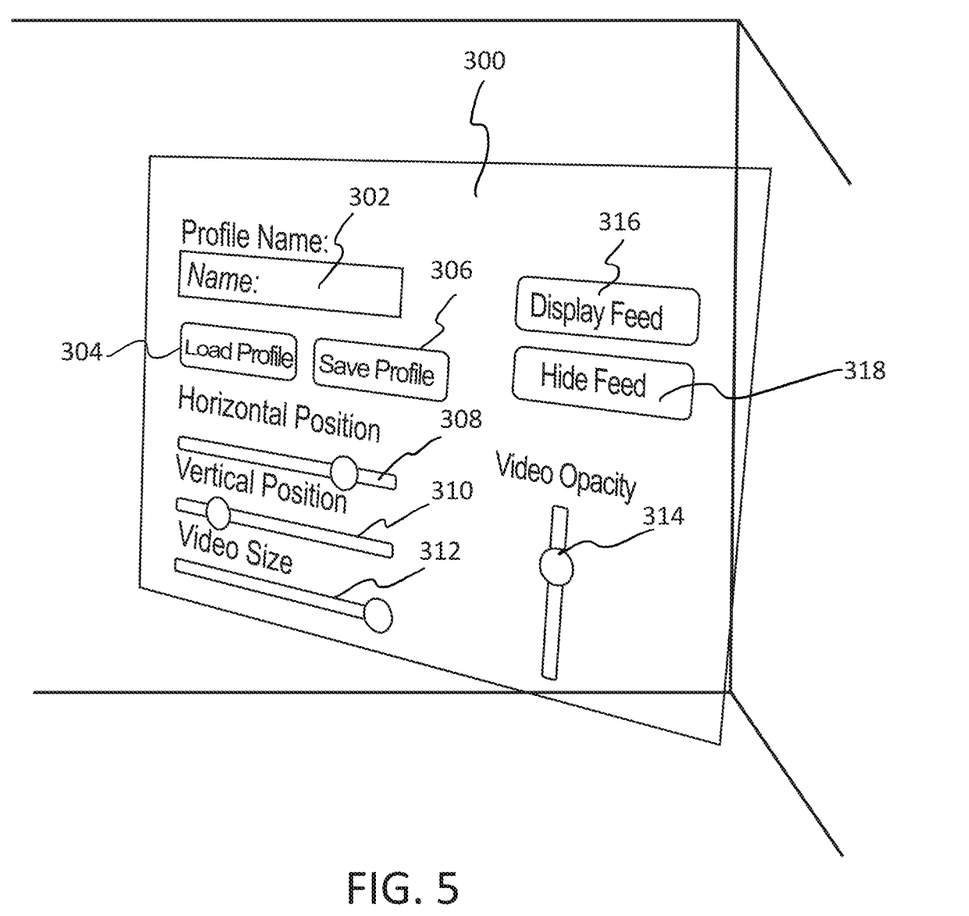
FIG. 5 depicts a user perspective of an embodiment of an augmented reality menu for customization of the manner in which a two-dimensional representation of video data is presented to a user three-dimensional space.

Accordingly, the two-dimensional representation 260 may be positionable within the three-dimensional space 250 by customization of the two-dimensional display 260. With further reference to FIG. 5, an example of a menu 300 that is presented to the user 200 by the augmented reality display device 130 is shown. The menu 300 may be utilized by the user 200 to customize the position or other characteristics of the two-dimensional representation 260 within the three-dimensional environment 250.

For instance, the two-dimensional representation 260 may be virtually moved in at least one degree of freedom within the three-dimensional environment 250. In a preferred embodiment, the two-dimensional representation 260 may be moved along any one of a first translational degree of freedom 262, a second translational degree of freedom 264, or a third translational degree of freedom 266. Furthermore, the two-dimensional representation 260 may be rotated about a first rotational degree of freedom 268, a second rotational degree of freedom 270, or a third rotational degree of freedom 272. Further still, an overall size of the two-dimensional representation 260 may be controlled by the user 200. In addition, an opacity of the two-dimensional representation 260 may be varied.

As may be appreciated, the foregoing adjustments to the two-dimensional representation 260 may be adjusted by the user 200 using the menu 300. In this regard, a set of parameters regarding the two-dimensional representation 260 may be saved as a profile. In this regard, the menu 300 may allow for naming of the profile and a profile name field 302 may be provided for entering the profile name. A user may elect to save a profile by selection of a save profile button 306. In turn, the user may select a given profile by selection of the load profile button 304. The menu 300 may allow for adjustment of the two-dimensional representation 260 within the three-dimensional environment 250 by selection of a horizontal position slider 308 which may correspond to one of the translational degrees of freedom described above. Moreover, a vertical position slider 310 may be manipulated by the user to adjust the two-dimensional representation 260 in a second translational degree of freedom. While further adjustment in additional translational degrees of freedom and/or rotational degrees of freedom is not shown in menu 300, it may be appreciated that a similar adjustment selection in the menu 300 may be provided to control the two-dimensional representation 260 in these additional translational degrees of freedom or rotational degrees of freedom as described above. Furthermore, the video size may be controlled by a video size slider 312. Additionally, the video opacity may be controlled by the slider 314. In addition, the menu 300 may present a display feed selection 316 that allows the two-dimensional representation 260 to be displayed. Should the user 200 wish to remove the two-dimensional representation 260 from the field of view, a hide feed button 318 may be selected.

In the foregoing discussion, selection and manipulation of the various menu items 300 may be accomplished by any appropriate means. This may include utilization of gestures by the user 200 to interact with the menu 300 by selection of the various menu items utilizing gestures by the user 200. Further still, traditional input devices such as a mouse, touchscreen device, keyboard, or other input means may also or alternatively be utilized for manipulation of the menu 300 by the user.

While not shown, an option may be presented to the user that allows for capture of video data and/or augmented reality session data for storage (e.g., on the host computer 120). In this regard, the medical imaging data provided to the augmented reality engine 122 may be stored in memory for later retrieval. In addition, the augmented reality session including the manner in which the medical imaging data is presented to the user during the session may also be recorded such that the entire augmented reality session may be later retrieved to provide information regarding what the user viewed during the session. Accordingly, information regarding the position of the two-dimensional representation 260 during this time may also be saved. Accordingly, the augmented reality session may later be reproduced for reproduction of the augmented reality session a further augmented reality session or for review in a virtual reality session in which the user is immersed in the augmented reality session stored.

Figure 6:
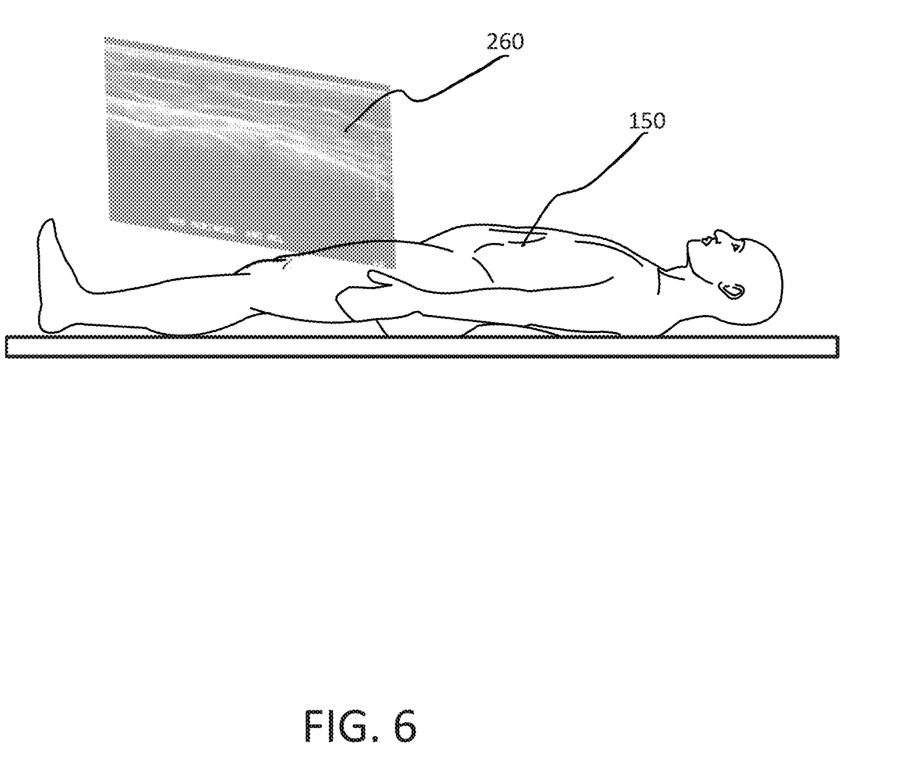
FIG. 6 depicts an embodiment of a user perspective of a two-dimensional video data presented relative to a three-dimensional patient using an augmented reality display device.

With reference to FIG. 6, it may be appreciated that the two-dimensional representation 260 may be position relative to the patient 150 by the user 200 when performing medical care on the patient 150. A user may adjust the two-dimensional representation 260 of the medical imaging data relative to the patient 150 in any manner appropriate or desired by the user. This may include positioning the two-dimensional representation 260 of the medical imaging data adjacent to the patient 150 such that the two-dimensional representation 260 of the medical imaging data is positioned adjacent to the patient 150 for easy reference by the user 200.

An alternative approach, the two-dimensional representation 260 may be selectively positioned by the user 200 such that the two-dimensional representation 260 is superimposed over relevant anatomic portion of the patient 150 to assist and guidance of a medical procedure or provision of medical care by the user 200. In this regard, the two-dimensional representation 260 may be provided in a fixed relative position within the three-dimensional environment 250 such that the two-dimensional representation 260 remain stationary within the three-dimensional environment 250 as placed by the user 200. An alternative approach, the two-dimensional representation 260 may be positioned with reference to the user is positioned to hundred such that as the user 200 moves their field of view, the two-dimensional representation 260 is fixed within the field of view.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. An augmented reality system for presentation of real-time medical imaging data to a user, comprising:
   an augmented reality engine executed by a processor and in direct operative communication with a video data output of a medical imaging device and in operative communication with an augmented reality display device;
   a data ingestion script executable by the processor of the augmented reality engine for receipt of the video data output of the medical imaging device in real time, wherein the data ingestion script executes without a data cache in which the video data output is stored prior to processing for communication to the augmented realty display device; and
   a video manipulation module operative to control at least a position of a two-dimensional representation of the video data output in a three-dimensional space relative to the augmented reality display device at least with respect to one degree of translational freedom and at least with respect to at least one rotational degree of freedom in the three-dimensional space.

2. The augmented reality system of claim 1, wherein the data ingestion script receives directly the video data output from a graphics card of the medical imaging device without intervening processing.

3. The augmented reality system of claim 1, wherein the medical imaging device comprises one of an ultrasound device, an MRI device, or a CT device.

4. The augmented reality system of claim 1, wherein the medical imaging device comprises an ultrasound device.

5. The augmented reality system of claim 1, wherein the data ingestion script is operative to receive the video data output in a format corresponding to a video interface.

6. The augmented reality system of claim 5, wherein the video interface comprises at least one of DVI, HDMI, or VGA.

7. The augmented reality system of claim 1, wherein the video manipulation module is operative to control the position of the two-dimensional representation of the video data output in at least two translational degrees of freedom in the three-dimensional space.

8. The augmented reality system of claim 1, wherein the video manipulation module is operative to control the position of the two-dimensional representation of the video data output in at least three translational degrees of freedom in the three-dimensional space.

9. The augmented reality system of claim 1, wherein the video manipulation module is operative to control the position of the two-dimensional representation of the video data output in at least two rotational degrees of freedom in the three-dimensional space.

10. The augmented reality system of claim 1, wherein the video manipulation module is operative to control the position of the two-dimensional representation of the video data output in at least three rotational degrees of freedom in the three-dimensional space.

11. The augmented reality system of claim 1, wherein the video manipulation module is operative to control a size of the two-dimensional representation of the video data output in the three-dimensional space.

12. The augmented reality system of claim 1, wherein the video manipulation module is operative to control an opacity of the two-dimensional representation of the video data output in the three-dimensional space.

13. The augmented reality system of claim 1, further comprising:
a virtual reality display device comprising a wearable display positionable in a visual field of a user wearing the virtual reality display, wherein the virtual reality display is operative to display to the user the two-dimensional representation of the video data output.

14. The augmented reality system of claim 1, wherein the video manipulation module is operative to generate a menu for display in the three-dimensional space for receipt of user inputs to control at least the position of the two-dimensional representation of the video data output in the three-dimensional space.

15. A method for presenting medical imaging data to a user in an augmented reality environment, comprising:
receiving video data output at a data ingestion script of an augmented reality engine via direct communication with a medical imaging device in real time;
processing the video data output by the augmented reality engine in real time in a cacheless environment;
determining a position of a two-dimensional representation of the video data output in a three-dimensional space relative to an augmented reality display device, wherein the determining comprises controlling the position of the two-dimensional representation of the video data output in the three-dimensional space in at least one degree of translational freedom and at least with respect to at least one rotational degree of freedom in the three-dimensional space; and
communicating data corresponding to the two-dimensional representation of the video data output to the augmented reality display device.

16. The method of claim 15, wherein the determining comprises controlling the position of the two-dimensional representation of the video data output in the three-dimensional space in three degrees of translational freedom.

17. The method of claim 15, wherein the determining comprises controlling the position of the two-dimensional representation of the video data output in the three-dimensional space in three degrees of rotational freedom.

18. The method of claim 15, further comprising:
controlling a size of the two-dimensional representation of the video data output in the three-dimensional space.

19. The method of claim 15, further comprising:
controlling an opacity of the two-dimensional representation of the video data output in the three-dimensional space.

20. The method of claim 15, further comprising:
presenting a menu to a user via the augmented reality display device, wherein the menu comprises at least one interactive element corresponding to the position of the two-dimensional representation of the video output data in the three-dimensional space;
receiving a user selection regarding the position of the two-dimensional representation of the video output data in the three-dimensional space; and
outputting data corresponding to the user selection to the augmented reality display device.

21. A non-transitory computer readable medium comprising machine readable instructions, that when executed by a processor of an augmented reality engine, cause the processor to:
receive video data output at a data ingestion script of an augmented reality engine via direct communication with a medical imaging device in real time;
process the video data output by the augmented reality engine in real time in a cacheless environment;
determine a position of a two-dimensional representation of the video data output in a three-dimensional space relative to an augmented reality display device, wherein the determining comprises controlling the position of the two-dimensional representation of the video data output in the three-dimensional space in at least one degree of translational freedom and at least with respect to at least one rotational degree of freedom in the three-dimensional space; and
communicate data corresponding to the two-dimensional representation of the video data output to the augmented reality display device.

* * * * *